United States Patent [19]

Suganuma et al.

[11] 3,981,989

[45] Sept. 21, 1976

[54] ORAL PREPARATION

[75] Inventors: Nobuo Suganuma, Funabashi; Kunio Saito, Kasukabe; Masaki Koshimizu, Chiba; Nobuyuki Takada, Chigasaki; Reiko Takamuro, Tokyo, all of Japan

[73] Assignee: The Lion Dentifrice Co., Ltd., Tokyo, Japan

[22] Filed: Jan. 21, 1976

[21] Appl. No.: 651,178

Related U.S. Application Data

[63] Continuation-in-part of Ser. No. 481,230, June 20, 1974, abandoned.

[30] Foreign Application Priority Data

Nov. 26, 1973 Japan.............................. 48-131648

[52] U.S. Cl.................................. 424/50; 424/52; 424/57; 424/94
[51] Int. Cl.² ....................... A61K 7/18; A61K 7/28
[58] Field of Search..................................... 424/50

[56] References Cited

UNITED STATES PATENTS

| | | | |
|---|---|---|---|
| 1,470,794 | 10/1923 | Andresen | 424/54 |
| 3,737,383 | 6/1973 | Abe et al. | 424/50 |

FOREIGN PATENTS OR APPLICATIONS

| | | | |
|---|---|---|---|
| 1,925,982 | 11/1970 | Germany | 424/50 |
| 285,956 | 2/1928 | United Kingdom | 424/55 |

OTHER PUBLICATIONS

Dixon et al. Enzymes, Acad. Press N.Y. (1958) pp. 45, 153, 493.

*Primary Examiner*—Shep K. Rose
*Attorney, Agent, or Firm*—Oblon, Fisher, Spivak, McClelland & Maier

[57] ABSTRACT

An oral composition effective in the prevention of tooth decay is prepared by combining dextranase and gelatin or peptone in a nontoxic vehicle.

8 Claims, No Drawings

ORAL PREPARATION

CROSS-REFERENCE TO RELATED APPLICATIONS

This application is a continuation-in-part of application Ser. No. 481,230, filed June 20, 1974, now abandoned.

BACKGROUND OF THE INVENTION

1. Field of the Invention

The present invention relates to an improved oral preparation containing dextranase which promotes oral hygiene.

More particularly, this invention relates to stabilized dextranase in the oral preparation.

2. Description of the Prior Art

Heretofore, fluoride compounds, phosphate compounds, antienzymes, germicides, neutralizing agents and the enzyme dextranase, have been added to oral preparations as active ingredients for preventing tooth decay. However, plaque which is formed and adheres to teeth, is composed of various bacteria and viscous material formed by the bacteria. This viscous material is mainly composed of dextran and polysaccharides which adhere to the tooth surface, and is decomposed by the bacteria in the plaque to produce organic acids. The enamel and dentin of the tooth are dissolved by the organic acids and tooth decay results.

In conventional oral preparations containing dextranase, the enzyme is easily deactivated by anionic surfactants and water contained in the oral preparation.

A need exists therefore for a stabilized enzyme-containing oral preparation.

SUMMARY OF THE INVENTION

Accordingly, one object of this invention is to provide an oral preparation for the prevention of tooth decay.

Another object is to provide an oral preparation which contains stabilized dextranase.

A further object is to provide an oral preparation containing a long-lived active ingredient.

These and other objects of the invention as will hereinafter become more readily understood by the following description can be attained by an oral preparation containing dextranase combined with a special proteinaceous enzyme stabilizer such as gelatin or peptone which prolongs and activates the effect of the dextranase.

DETAILED DESCRIPTION OF THE PREFERRED EMBODIMENTS

In the oral preparation of the invention, dextranase is combined with a special protein such as gelatin or peptone, whereby the lifetime of the dextranase is enhanced. When gelatin is used, an oral preparation results in which the dextranase becomes activated, and which has an excellent preventive effect against tooth decay. The oral preparation also imparts an improved cleaning effect by removing plaque without adversely affecting the desirable characteristics of the oral preparation. The preparation removes mouth odor, prevens tartar formation and adhesion of bacteria on tooth surfaces, decreases the amount of viscous material in the mouth, and produces a satisfactory fresh feeling.

The gelatin or peptone is preferably added to the extent of 0.3 – 3% by weight. Sodium monofluorophosphate is also preferably added to the preparation. The tooth decay inhibition effect of sodium monofluorophosphate is promoted by the dextranase, since dextranase removes stains on the tooth surfaces and allows more intimate contact of sodium monofluorophosphate with the clean tooth surfaces.

When water soluble inorganic phosphates such as ammonium phosphate, sodium phosphate, sodium pyrophosphate, or the like are combined with the sodium monofluorophosphate, the effect of the sodium monofluorophosphate is enhanced, and the stability of the dextranase is promoted. Accordingly, the dextranase is preferably combined with a special protein such as gelatin or peptone, sodium monofluorophosphate, and a water soluble phosphate, to form the oral preparation. Preferable amounts of these ingredients are 0.05 – 0.76% by weight of sodium monofluorophosphate and 0.1 – 20% by weight of the water soluble phosphate.

Nonionic surfactants such as alkyloldiethanolamides, monoethanolamides, sugar esters, polyoxyethylenesorbitane laurate or the like may also be added to impart stability to the dextranase. The nonionic surfactant is usually added with an anionic surfactant such as sodium laurylsulfate or sodium lauroyl sarcosinate. The amount of the nonionic surfactant is preferably about 5 – 100% of the total surfactant.

Sodium acyltaurate is another suitable anionic surfactant which promotes the stability of the dextranase in the oral preparation and is preferably present to the extent of 0.5 – 5% by weight of the oral preparation.

The dextranase may be prepared by inoculating Chaetomium gracile or Penicillium fuiculosum into a medium containing dextran, and separating the enzyme by conventional methods. The amount and activity of the dextranase used in the oral preparation should be sufficient to effectively promote oral hygiene. The activity is preferably 10 – 200,000,000 units/g of dextranase and more preferably 500,000 – 1,500,000 units/g of dextranase. The amounts of dextranase to be used should be 5,000 to 1,500,000 preferably 5,000 to 150,000 units per gram of the oral preparation. Of course, the total weight of the dextranase to be used will depend on its activity. Typically the weight percentage of detranase in the oral preparation will be from 0.1 – 10 wt %, preferably 0.5 – 5 wt %, and especially 0.7 – 3.0 wt %. When less than 5,000 units of dixtranase per gram of the oral preparation is used, the resultant effect of this invention is inferior. When more than 1,500,000 units of dextranase per gram of the oral preparation is used, the increased cost becomes economically disadvantageous. When 5,000 to 1,500,000 units of dextranase per gram of oral preparation are used the results of this invention are obtained.

EXPERIMENTAL METHOD

In order to stabilize dextranase, various additives, including a polysaccharide and proteins were added to a typical oral preparation together with the dextranase. The effects of the additives on the stability of the dextranase were studied.

The activity of the dextranase was measured by the 3,5-dinitrosalicylic acid method, wherein 1 unit designates the degree of color corresponding to 1 $\mu$g of glucose per 1 minute at 35°C. The formula of the control oral preparation used in the tests is as follows:

| | |
|---|---|
| Dicalcium phosphate dihydrate | 50 wt % |
| Sorbitol | 20 |
| Carrageenan | 1 |
| Saccharin | 0.1 |
| Sodium lauryl sulfate | 1.2 |
| Lauryldiethanolamide | 0.5 |
| Flavor | 0.8 |
| Dextranase (820,000 unit/g) | 2 |
| Sodium monofluorophosphate | 0.76 |
| Water | balance |
| Total | 100 wt % |

EXPERIMENTAL RESULTS

The residual percent activity of the dextranase was measured for each oral preparation containing each additive. The results are shown in Table 1.

TABLE 1

| Additive | | Activity at the time of preparation ($\mu$g) | Residual rate of activity at 30°C for 30 days (%) |
|---|---|---|---|
| Type | % Amount | | |
| none | — | 315 | 78.0 |
| CaCl$_2$ | 0.5 | 308 | 74.0 |
| Starch | 0.5 | 308 | 65.3 |
| Dextran | 0.5 | 336 | 76.5 |
| Vitamin B$_1$ | 0.5 | 319 | 63.6 |
| Albumin | 0.5 | 334 | 79.3 |
| Casein | 0.5 | 349 | 78.2 |
| Gelatin | 0.5 | 375 | 100.5 |
| Peptone | 0.5 | 334 | 91.9 |

In the results shown in Table 1, the residual amount of dextranase at 30°C for 30 days in the oral preparation containing gelatin and peptone was markedly higher than those containing other additives or no additive to act as a stabilizer. A high residual amount of dextranase would be necessary for long storage of the oral preparation. The residual amount of dextranase in the oral preparation containing gelatin or peptone after 105 days was still quite high, 89% and 80% respectively, so that such preparations are excellently suitable for long-term storage. The long-term residual amount of dextranase in the oral preparation containing both gelatin and peptone is superior to those containing other additives.

The enhanced activity of the dextranase by combination of gelatin in the oral preparation is unexplainable. In an oral preparation containing dextranase corresponding to 330 $\mu$g of glucose as a theoretical amount, the activity of the dextranase of the control was 315 $\mu$g at the time of preparation. By adding gelatin, the activity of the dextranase of the oral preparation increased to 375 $\mu$g. The gelatin does not produce reducing agents and thus promotes the activity of the dextranase. The oral preparations containing no gelatin (control) and containing gelatin were prepared repeatedly, and the activity of the dextranase was measured at the time of preparation. The average activity of the dextranase of the control was 328 $\mu$g while that of the oral preparation containing gelatin was 371 $\mu$g. Accordingly, the effect of increasing the activity of the dextranase by gelatin was confirmed. The amount of gelatin or peptone added is usually 0.1 – 5%, preferably 0.3 – 3%, to produce stabilization of the dextranase, good feeling in the mouth, and stability of the oral preparation.

Suitable oral preparations of the present invention include dental creams, tooth powders, liquid dentifrices, mouth washes, chewing gums, dental floss, troches, or the like. Suitable dentifrices may be prepared by employing polyalcohols, such as glycerin, sorbitol or the like, polishing agents such as dicalcium phosphate, calcium carbonate, calcium pyrophosphate, insolube sodium metaphosphate, anhydrous silica, or the like; binders, such as sodium carboxymethylcellulose sodium alginate, carrageenan; anionic surfactants, such as sodium laurylsulfate, laurylmonoglyceride sulfate, olefin sulfonates, acyltaurate, lauryl-monoglyceride sulfonate, isothionate, or lauroylsarcosinate; nonionic surfactants, such as lauryldiethanolamide, sugar esters, stearyl-monoglyceride, polyoxyethylene sorbitan monolaurate, or the like, amphoteric surfactants, sweetening agents, flavors, such as menthol, anethole, or the like; sodium monofluorophosphate, stannous fluoride, sodium fluoride, sodium phosphate, germicides, and water.

A dental cream formulation can be composed of a nontoxic vehicle of 20 – 70 wt % of a polishing agent, 20 – 70 wt % of water and polyalcohol liquid components, 0.2 – 10 wt % of a binder, 0.05 – 5 wt % of a surfactant and 0.05 – 5 wt % of a flavoring agent which is combined with 5,000 to 1,500,000 units of dextranase per gram of the oral preparation and 0.3 – 3 wt % of gelatin or peptone.

The ratios of the basic components of the dentifrices, especially dental cream, are clearly known in the prior art and can be easily selected by a person skilled in the art. Accordingly, a detailed description of the basic components has been omitted from the specification.

Having generally described the invention, a more complete understanding can be obtained by reference to certain specific examples, which are included for purposes of illustration only and are not intended to be limiting unless otherwise specified.

EXAMPLE 1

A dental cream was prepared by combining the following components and was placed into a collapsible aluminum tube.

| Dental Cream | wt. % |
|---|---|
| Dicalcium phosphate dihydrate | 50 |
| Sorbitol | 20 |
| Sodium laurylsulfate | 1.5 |
| Sodium alginate | 1 |
| Saccharin | 0.1 |
| Sodium monofluorophosphate | 0.76 |
| Flavor | 1 |
| Gelatin | 0.5 |
| Dextranase (800,000 unit/g) | 2 |
| Water | balance |
| Total | 100 wt % |

EXAMPLE 2

| Tooth Powder | wt % |
|---|---|
| Dicalcium phosphate dihydrate | 50 |
| Calcium carbonate | 25 |
| Glycerine | 10 |
| Sodium olefin sulfonate | 2 |
| Saccharin | 0.1 |
| Sodium phosphate | 1 |
| Flavor | 1 |
| Peptone | 0.3 |
| Dextranase (1,000,000 unit/g) | 1 |
| Water | balance |
| Total | 100 wt % |

EXAMPLE 3

| Liquid Dentifrice | wt % |
|---|---|
| Glycerine | 35 |
| Sodium polyacrylate | 5 |
| Sodium laurylsulfate | 2 |
| Lauryldiethanolamide | 0.5 |
| Saccharin | 0.1 |
| Alcohol | 1 |
| Flavor | 1 |
| Gelatin | 1 |
| Dextranase (500,000 unit/g) | 2 |
| Water | balance |
| Total | 100 wt % |

EXAMPLE 4

| Mouth Wash | wt % |
|---|---|
| Ethanol (90%) | 20 |
| Saccharin | 0.3 |
| Sodium acyltaurate | 0.5 |
| Flavor | 1 |
| Gelatin | 0.5 |
| Peptone | 0.2 |
| Dextranase (500,000 unit/g) | 3 |
| Water | balance |
| Total | 100 wt % |

EXAMPLE 5

| Troche | wt % |
|---|---|
| Gum arabic | 6 |
| Dextrose | 72 |
| Flavor | 1 |
| Gelatin | 3 |
| Dextranase (1,000,000 unit/g) | 2 |
| Water | balance |
| Total | 100 wt % |

EXAMPLE 6

| Chewing Gum | wt % |
|---|---|
| Gum Base | 20 |
| Calcium carbonate | 2 |
| Dextrin + glucose (1 : 1) | 15 |
| Sugar | 60 |
| Flavor | 1 |
| Peptone | 0.3 |
| Dextranase (1,500,000 unit/g) | 0.7 |
| Total | 100 wt % |

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. An oral preparation which comprises a non-toxic vehicle and the combination of dextranase and gelatin or peptone, wherein the amount of dextranase in said oral preparation is 5000 – 1,500,000 units per gram of the oral preparation and wherein said gelatin or peptone is present in said oral preparation in amounts of 0.3 – 3 wt%.

2. The oral preparation of claim 1, which further comprises sodium monofluorophosphate.

3. The oral preparation of claim 1, which further comprises a nonionic surfactant.

4. The oral preparation of claim 1, which further comprises sodium acyltaurate.

5. The oral preparation of claim 1, which further comprises a water soluble phosphate.

6. The oral preparation of claim 1, wherein the non-toxic vehicle is a polishing agent, a polyalcohol, a detergent, a binder and water.

7. The oral preparation of claim 1, wherein said non-toxic vehicle comprises 20–70% by weight of a polishing agent, 20–70% by weight of total water and polyalcohol liquid components, 0.2 – 10% by weight of a binder, 0.05 – 5% by weight of a surfactant, and 0.05 – 5% by weight of a flavoring agent.

8. The oral preparation of claim 1, wherein the amount of dextranase in said oral preparation is 0.1 – 10 wt%.

* * * * *